United States Patent [19]

Le Tourneau et al.

[11] Patent Number: 4,734,429

[45] Date of Patent: Mar. 29, 1988

[54] CYCLOALKANE[1,2-c:4,3-C']DIPYRAZOLES AND THEIR USE AS BRONCHODILATORS

[75] Inventors: Michael E. Le Tourneau; Norton P. Peet, both of Indianapolis, Ind.

[73] Assignee: Merrell Dow Pharmaceuticals Inc., Cincinnati, Ohio

[21] Appl. No.: 7,304

[22] Filed: Jan. 27, 1987

[51] Int. Cl.$^4$ .................. A61K 31/415; C07D 231/54; C07D 231/56
[52] U.S. Cl. ........................... 514/406; 548/369
[58] Field of Search .................. 548/371, 369; 514/406

[56] References Cited

U.S. PATENT DOCUMENTS 3,404,157 10/1968 McEvoy et al. ............... 548/371
4,515,948 5/1985 Kompis et al. ............... 544/253

OTHER PUBLICATIONS

C. Ruchardt, V. Hassmann, *Liebigs Ann. Chem.*, 6:908–27 (1980).
*Heterocyclic Compounds*, vol. 5, R. C. Elderfield, ed., John Wiley & Sons, Inc., New York, N.Y., 1957, p. 173.
Beilstein, 4th ed., vol. 26, 579, J. U. Nef, *Liebigs Annalen Der Chemie*, 258:261 (1890).
V. Vesely, A. Medvedeva, Collection Czechoslav *Chem. Commun.*, 9:176–84 (1937).

*Primary Examiner*—Henry R. Jiles
*Assistant Examiner*—Kurt G. Briscoe
*Attorney, Agent, or Firm*—John J. Kolano

[57] ABSTRACT

The present invention is directed to a group of methylated tetrahydro cyclohepta[1,2-c:4,3-c']dipyrazoles and benzo[1,2-c:4,3-c']dipyrazoles useful as bronchodilators. The compounds are prepared by the reaction of an appropriate hydrazine with an appropriate 1,3-diketone or with a compound that is chemically equivalent to a 1,3-diketone.

7 Claims, No Drawings

CYCLOALKANE[1,2-C:4,3-C']DIPYRAZOLES AND THEIR USE AS BRONCHODILATORS

The present invention is directed to a group of compounds which are methylated tetrahydro cyclohepta[1,2-c:4,3-c']dipyrazoles and benzo[1,2-c:4,3-c']dipyrazoles. More particularly, the present invention is directed to a group of compounds having the formula:

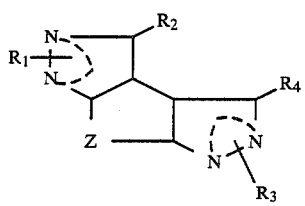

wherein $R_1$, $R_2$, $R_3$ and $R_4$ are each independently selected from hydrogen or methyl with the proviso that at least one of them must be methyl and with $R_1$ and $R_3$ being positioned on one of the nitrogens in their respective rings with the other nitrogen then being doubly bonded to the adjacent carbon; the dotted lines indicate the presence of two conjugated double bonds with the specific position of the double bonds being determined by the position of the $R_1$ or $R_3$ substituents; and Z is —$(CH_2)_n$— wherein n is 2 or 3. The present invention further encompasses the pharmaceutically acceptable acid addition salts of the aforesaid compounds.

Acid addition salts of the aforesaid compounds with pharmaceutically acceptable acids are equivalent to the above amines for the purposes of this invention. Illustrative of such salts are the salts with inorganic acids such as, for example, hydrochloric, hydrobromic, sulfuric, phosphoric and like acids; with organic carboxylic acids such as, for example, acetic, propionic, glycolic, lactic, pyruvic, malonic, succinic, fumaric, malic, tartaric, citric, ascorbic, maleic, hydroxymaleic and dihydroxymaleic, benzoic, phenylacetic, 4-aminobenzoic, 4-hydrobenzoic, anthranilic, cinnamic, salicylic, 4-aminosalicyclic, 2-phenoxybenzoic, 2-acetoxybenzoic, mandelic and like acids; and with organic sulfonic acids such as methanesulfonic acid and p-toluenesulfonic acid.

Preferred embodiments of the present invention are those compounds wherein Z is —$(CH_2)_3$—.

The compounds of the present invention are prepared by the reaction of a hydrazine of the formula

$R_1$—NHNH$_2$ wherein $R_1$ is hydrogen or methyl, with an α-substituted cyclic ketone of the formula

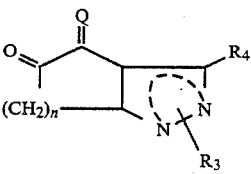

wherein $R_3$ and $R_4$ are each independently hydrogen or methyl; n is 2 or 3; and Q is =(H)(COCH$_3$) or =CHN(CH$_3$)$_2$. The reaction is carried out with heating in an inert solvent such as an alcohol, with methanol being preferred. When Rhd 1 or $R_3$ is hydrogen, the product is further optionally treated with sodium hydride and methyl iodide in an inert solvent such as N,N-dimethylformamide to give the corresponding compounds wherein Rhd 1 or $R_3$ is methyl. When the process gives a mixture of product with substitution on either nitrogen in the rings in question, the resultant mixture is separated by chromatography.

The α-substituted cyclic ketone used as the starting material for the cycloheptadipyrazoles (n=3) can be prepared from cyclohexane-1,3-dione. This diketone can be converted to the corresponding 2-dimethylaminomethylene compound by standard procedures. Reaction of this material with an appropriate hydrazine (i.e., hydrazine or methylhydrazine) brings about cyclization and formation of an indazol-4-one which may be substituted on one of the nitrogens depending on the hydrazine starting material used. The indazolone is reacted with ethyl diazoacetate to introduce a methylene group alpha to the carbonyl. A mixture of products is obtained with the major product having a methylene introduced between the carbonyl and the pyrazole ring. This ketone is then reacted with the appropriate reagents to give the desired α-substituted ketone starting material; N,N-dimethylformamide dimethyl acetal specifically gives the α-dimethylaminomethylene compound.

The α-substituted cyclic ketone used as the starting material for the benzodipyrazoles (n=2) can be prepared from 1,4-cyclohexanedione monoethylene ketal by the following series of reactions:

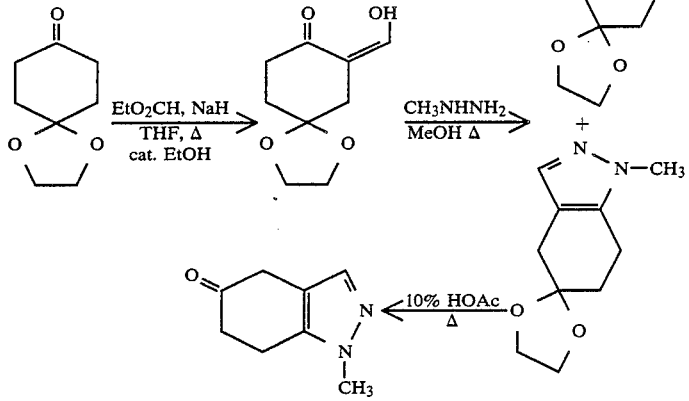

The cyclohexanedione ketal is treated with sodium hydride and ethyl formate to provide the α-formyl compound which is then reacted with methylhydrazine to give a mixture of isomeric pyrazoles. The ratio of isomers obtained is greatly influenced by the reaction temperature. For example, if methylhydrazine is added to a solution of α-formyl compound in methanol at reflux, the two isomers are obtained in about a 1:1 ratio. However, if methylhydrazine is added dropwise to an ice-cold solution of α-formyl compound in methanol, the 1-methyl product is formed almost exclusively. Deketalization of the spiro compound proceeded smoothly in 10% acetic acid at reflux to provide the indicated ketone. The ketone is then converted to the desired α-substituted cyclic ketone in the same way as described earlier for the cycloheptapyrazolone.

The substituted dipyrazole compounds as described herein are bronchodilators and are thus useful in the treatment of bronchial disorders such as bronchial asthma. The present invention is further directed to a method of effecting bronchodilation.

In practicing the method of this invention, an effective bronchodilating amount of 1 or more substituted dipyrazoles of this invention is administered internally to a mammal in need thereof by a route effective to bring the compound into contact with the bronchial and tracheal tissues of the mammal. Administration can be carried out either by a parenteral route, such as by intravenous, intraperitoneal or intramuscular injection, or by introduction into the gastrointestinal tract via oral or rectal administration, for example, in order to bring about such contact via the blood stream, or by intratracheal administration, by inhalation of a solution in the form of a spray, for example.

The effective bronchodilating amount of the compound, that is, the amount sufficient to inhibit or alleviate bronchial spasm, depends on various factors such as the size, type and age of the animal to be treated, the particular compound or pharmacologically-acceptable salt employed, the route and frequency of administration, the severity of any spasm and the causative agent involved, and the time of administration. In particular cases, the dosage to be administered can be ascertained by conventional range finding techniques, for example, by observing the bronchodilator activity produced at different dosage rates. More specifically, the compounds can be administered at dosage rates ranging from about 0.2 to about 100 milligrams of substituted dipyrazole compound per kilogram of animal body weight with other ranges being from about 0.5 to about 20 or from 1 to about 5 milligrams per kilogram. It is generally desirable to administer individual dosages at the lowest amount which provides the desired protection from bronchial spasm consonant with a convenient dosing schedule. Dosage units adaptable to oral administration such as tablets, capsules, lozenges, elixirs, syrups and the like are generally preferred and the active compound can be formulated in conventional time release capsule or tablet formulations although injectable compositions or sprays and aerosols for inhalation are preferred when rapid action is desired. In an example of an individual dosage unit, a tablet would contain 200 mg of active ingredient and would be administered 1 to 6 times daily or, preferably, 2 to 4 time daily.

In practicing the method of the invention, the active ingredient is preferably incorporated in a composition comprising a pharmaceutical carrier and from about 5 to about 90 percent by weight of the substituted dipyrazole compound or a pharmaceutically-acceptable salt thereof. The term "pharmaceutical carrier" refers to known pharmaceutical excipients useful in formulating pharmaceutically active compounds for internal administration to animals, and which are substantially non-toxic and non-sensitizing under conditions of use. The compositions can be prepared by known techniques for the preparation of tablets, capsules, lozenges, troches, suppositories, elixirs, syrups, emulsions, dispersions, wettable and effervescent powders, sterile injectable compositions and solutions for sprays, and can contain suitable excipients known to be useful in the preparation of the particular type of compositions desired. Suitable pharmaceutical carriers and formulation techniques are found in standard texts, such as *Remingington's Pharmaceutical Sciences,* Mack Publishing Company, Easton, Pa.

In evaluating bronchodilator activity, test compounds were administered to guinea pigs by intraperitoneal injection or orally and the guinea pigs were challenged by exposure to a histamine aerosol at periods ranging from 15 minutes to 4 hours later. Untreated animals collapsed when exposed to the histamine aerosol. In the operations, the animals were observed and collapse times were recorded. The collapse times observed were then compared statistically with control animals treated with water alone with the control group usually being a long-term cumulative control. The actual dose of test compound administered was generally 30% of the $LD_{50}$ administered intraperitoneally. Some specific doses of compounds used in the testing are as follows:

4,5,6,7-Tetrahydro-3-methyl-3H-cyclohepta[1,2-c:4,3-c']dipyrazole; 188 mg/kg.

4,5,6,7-Tetrahydro-2,7-dimethyl-2H-cyclohepta[1,2-c:4,3-c']dipyrazole; 315 mg/kg.

4,5,6,7-Tetrahydro-3,7-dimethyl-3H-cyclohepta[1,2-c:4,3-c']dipyrazole; 166 mg/kg.

3,4,5,6-Tetrahydro-3,6-dimethylbenzo[1,2-c:4,3-c']dipyrazole monohydrochloride; 188 mg/kg.

When tested by the above procedure, the compounds of the present invention were found to produce a bronchodilating effect.

The following examples are presented to illustrate the present invention but they should not be construed as limiting it in any way.

EXAMPLE 1

A mixture was prepared from 90 grams of 1,3-cyclohexanedione and 225 ml of N,N-dimethylformamide dimethyl acetal and heated at reflux for 90 minutes. Excess solvent was removed under reduced pressure and the residue was triturated in hot ethyl acetate to give 2-dimethylaminomethylene-1,3-cyclohexanedione as rust colored crystals melting at about 114.5°–116° C.

EXAMPLE 2

To an ice-cold solution of 67 grams of 2-dimethylaminomethylene-1,3-cyclohexanedione in 600 ml of methanol was added slowly a solution of 21.3 ml of methylhydrazine in 200 ml of methanol and the resulting solution was heated at reflux for 2 hours. The solvent was removed under reduced pressure and the residue was triturated with ethyl ether to give 1,5,6,7-tetrahydro-1-methyl-4H-indazol-4-one as a tan crystalline solid melting at about 88°–91° C.

To an ice-cold solution of 33.3 grams of 2-acetyl1,3-cyclohexanedione in 400 ml of methanol was added dropwise a solution of 7.2 ml of hydrazine in 50 ml of methanol and the resulting reaction mixture was heated at reflux for 20 hours. The solvent was then removed under reduced pressure and the residue was triturated in ethyl ether to give 1,5,6,7-tetrahydro-3-methyl-4H-indazol-4-one as a yellow crystalline solid melting at about 154°–157° C.

A solution of 11 ml of methylhydrazine in 50 ml of methanol was added dropwise to an ice-cold solution of 30 grams of 2-acetyl-1,3-cyclohexanedione in 200 ml of methanol and the reaction mixture was heated at reflux for 90 minutes. The solvent was removed under reduced pressure and the residue was triturated in hexane and cooled to give a clammy tan solid. This crude product was recrystallized from a mixture of toluene and hexane to give 1,5,6,7-tetrahydro-1,3-dimethyl-4H-indazol-4-one as a yellow crystalline solid melting at about 82.5°–84° C.

EXAMPLE 3

A solution of 108 ml of boron trifluoride etherate in 300 ml of dichloromethane was added dropwise to a solution of 79.3 g of 1,5,6,7-tetrahydro-1-methyl-4H-indazol-4-one and 100 g of ethyl diazoacetate in 1500 ml of dichloromethane. The rate of the addition was adjusted so that the temperature of the reaction mixture did not exceed 25° C. and the evolution of gas did not become vigorous. The addition took 3.5 hours and the reaction mixture was then stirred at room temperature, cooled to 0° C., and treated dropwise with 1000 ml of saturated aqueous sodium bicarbonate solution. The resulting slurry was stirred briefly and the layers which formed on standing were separated. The organic layer was washed with brine and dried over magnesium sulfate and the solvent was removed under reduced pressure to leave an amber oil. The oil was dissolved in dichloromethane and washed with 2.5M sodium hydroxide (two 300-ml portions). The dichloromethane solution was dried over magnesium sulfate and concentrated under reduced pressure to leave an amber oil. This oil was flash chromatographed (10% acetone in dichloromethane) to provide a further amber oil. This oil was treated with 24 g of potassium hydroxide an 300 ml of water and the mixture was heated in a boiling-water bath for 30 minutes. 5N Hydrochloric acid was added slowly until the pH was 2. The mixture was then heated briefly in a boiling-water bath and poured over ice. It was then neutralized with saturated sodium bicarbonate and extracted exhaustively with dichloromethane The combined extracts were dried over magnesium sulfate and the solvent was removed under reduced pressure to provide a dark oil which was heated at reflux with 60 ml of N,N-dimethylformamide dimethyl acetal for 2 hours. The solvent was removed under reduced pressure and the residue was flash chromatographed (10% acetone in dichloromethane) to give 5,6,7,8-tetrahydro-4(1H)-cycloheptapyrazolone as a red crystalline solid.

The combined sodium hydroxide extracts obtained during the initial stages of the isolation procedure described above were cooled to 0° C. and acidified to pH 5 with concentrated hydrochloric acid. The resulting slurry was extracted exhaustively with dichloromethane and the combined extracts were dried over magnesium sulfate and concentrated under reduced pressure to give an amber oil. The oil was treated with 45.8 g of potassium hydroxide in 600 ml of water and the mixture was heated in a boiling-water bath for 30 minutes. The reaction mixture was removed from the bath, acidified with 5N hydrochloric acid to a pH 2, heated in a boiling-water bath briefly, cooled in an ice bath and finally neutralized with saturated aqueous sodium bicarbonate solution. The resulting slurry was extracted thoroughly with dichloromethane and the combined extracts were dried over magnesium sulfate. The solvent was then removed under reduced pressure to give 4,6,7,8-tetrahydro-1-methyl-5(1H)-cycloheptapyrazolone as an amber oil.

EXAMPLE 4

1,4-Cyclohexanedione monoethylene ketal (5.00 g) was added to a mixture of sodium hydride (1.40 g of a 60% suspension in mineral oil), 10 ml of ethyl formate, 1 drop of ethanol and 200 ml of tetrahydrofuran. The reaction mixture was heated at reflux for 2.5 hours, cooled and partitioned between water and ethyl ether.

The ethereal layer was extracted several times with 0.5N sodium hydroxide and the combined aqueous portions were washed once with ether. The aqueous solution was acidified slowly to a pH of 4 with 5N hydrochloric acid and the slurry was exhaustively extracted with dichloromethane. The combined extracts were dried over magnesium sulfate and concentrated in vacuo to provide a dark oil. The oil was distilled bulb-to-bulb (120° C./1mm) to afford 7-(hydroxymethylene)-1,4-dioxaspiro-[4.5]decan-8-one as a colorless oil.

EXAMPLE 5

Methylhydrazine (0.6 ml) was added dropwise to an icecold solution of 2 g of 7-(hydroxymethylene)-1,4-dioxaspiro[4.5]decan-8-one. The solution was heated at reflux for 30 minutes and concentrated in vacuo to afford an amber oil. The oil was flash chromatographed (ethyl acetate) on silica gel to provide 1', 4', 6', 7'-tetrahydro-1'-methylspiro [1,3-dioxolane-2,5'-[5H]indazole]as a yellow oil.

The product obtained above (3.7 g) was heated in 100 ml of 10% acetic acid at reflux for 3 hours and the solvent was removed in vacuo to provide a dark oil. The oil was flash chromatographed (ethyl acetate) on silica gel to provide a mixture of 1,4,6,7-tetrahydro-1-methyl-5H-indazol-5-one and ethylene glycol. The ethylene glycol was removed by distillation (1 mm) to afford 1,4,6,7-tetrahydro-1-methyl-5H-indazol-5-one as an orange gum.

EXAMPLE 6

A mixture of 27.6 g of 4,6,7,8-tetrahydro-1-methyl-5(1H)-cycloheptapyrazolone and 100 ml of N,N-dimethylformamide dimethyl acetal was heated at reflux for 1.5 hours. The solvent was then removed under reduced pressure and the residue was flash chromatographed (10% methanol in dichloromethane) to give 4-(dimethylaminomethylene)-4,6,7,8-tetrahydro-1-methyl-5(1H)-cycloheptapyrazolone.

The above procedure was repeated using 1,4,6,7-tetrahydro-1-methyl-5H-indazol-5-one and N,N-dimethylformamide dimethyl acetal. The crude product was flash chromatographed (5% methanol in dichloromethane) on silica gel to give a thick amber oil which was triturated with etherhexane to give 4-(dimethylaminomethylene) 1,4,6,7-tetrahydro-1-methyl-5H-indazol-5-one as a tan powder melting at about 94°–100° C.

EXAMPLE 7

A solution of 1.75 ml of methylhydrazine in 30 ml of methanol was added dropwise to an ice-cold solution of 4-(dimethylaminomethylene)-4,6,7,8-tetrahydro-1-methyl-5(1H)cycloheptapyrozolone in 150 ml of methanol and the mixture was heated at reflux for 2 hours. The solvent was removed under reduced pressure and the residue was triturated with ether to give a yellow powder (68% yield). Recrystallization of this solid from toluene gave 4,5,6,7-tetrahydro-2,7-dimethyl-2H-cyclohepta[1,2-c:4,3-c']dipyrazole as colorless flakes melting at about 176°–178° C.

When the above procedure was repeated using hydrazine instead of methylhydrazine, the product obtained was 4,5, 6,7-tetrahydro-3-methyl-3H-cyclohepta[1,2-c:4,3-c']dipyrazole melting at about 201°–204° C.

EXAMPLE 8

A mixture of 19.4 g of 4,5,6,7-tetrahydro-3-methyl-3H-cyclohepta[1,2-c:4,3-c']dipyrazole in 70 ml of N,N-dimethylformamide was added, dropwise, to a suspension of 2.64 g of sodium hydride in 200 ml of N,N-dimethylformamide and the resulting mixture was stirred at room temperature for 15 minutes. A solution of 12.5 ml of methyl iodide in 20 ml of N,N-dimethylformamide was added dropwise and the reaction mixture was stirred at room temperature for 3 hours. The solvent was removed under reduced pressure and the residue was partitioned between dichloromethane and water. The aqueous layer was extracted several times with dichloromethane and the combined dichloromethane layers were washed with brine, dried over magnesium sulfate and concentrated under reduced pressure to give a tan powder which was shown to be a 50:50 mixture of the 2,7-dimethyl and 3,7-dimethyl products as shown by 1H NMR. The tan powder was recrystallized from toluene to give a tan solid which was again recrystallized from toluene to give 4,5,6, 7-tetrahydro-3,7-dimethyl-3H-cyclohepta[1,2-c:4,3-c']dipyrazole as tan needles melting at about 191°–195° C.

The combined mother liquors from the toluene recrystallizations were concentrated to half the original volume and cooled to give 4,5,6,7-tetrahydro-2,7-dimethyl-2H-cyclohepta[1,2-c:4,3-c']dipyrazole as a tan solid.

EXAMPLE 9

Hydrazine (1.00 ml) was added dropwise to a solution of 4.1 g of 4-[(dimethylamino)methylene]-1,4,6,7-tetrahydro-1-methyl-5H-indazol-5-one in 100 ml of methanol. The solution was heated at reflux for 30 minutes and treated with a small amount of activated charcoal. The mixture was gravity-filtered and the filtrate was concentrated in vacuo. The residue was flash chromatograhed (10% methanol in dichloromethane) on silica gel to provide an amber syrup. The syrup was triturated with ether to afford 3,4,5,6-tetrahydro-3-methylbenzo[1,2-c:4,3-c']dipyrazole as tan crystals (74% yield). Recrystallization from toluene gave a solid melting at about 150°–156° C.

EXAMPLE 10

A solution of 0.3 ml of methylhydrazine in 10 ml of methanol was added dropwise to an ice-cold solution of 1 g of 4-[(dimethylamino)methylene]-1,4,6,7-tetrahydro-1-methyl-5H-indazol-5-one in 30 ml of methanol. The solution was heated at reflux for 30 minutes and a small amount of decolorizing carbon was added. The mixture was filtered through diatomaceous earth and the filtrate was concentrated in vacuo to provide the crude product as a thick amber oil (87% yield). The oil was dissolved in 1:1 isopropanol:ethanol and treated with ethanolic hydrogen chloride. 3,4,5,6-Tetrahydro-3,6-dimethylbenzo[1,2-c:4,3-c']dipyrazole monohydrochloride was collected by filtra as a tan solid and recrystallized from isopropanol to give beige crystals melting at about 245°–249° C. with decomposition.

EXAMPLE 11

1,5,6,7-Tetrahydro-1,3-dimethyl-4H-indazol-4-one is reacted with ethyl diazoacetate according to the procedure described in Example 3 to give 4,6,7,8-tetrahydro-1,3-dimethyl-5(1H)-cycloheptapyrazolone. This is reacted with N,N-dimethylformamide dimethyl acetal according to the procedure described in the first paragraph of Example 6 to give 4-(dimethylaminomethylene)-4,6,7,8-tetrahydro-1,3-dimethyl-5(1H)-cycloheptapyrazolone. The dimethylaminomethylene compound is then reacted with hydrazine according to the procedure described in Example 7 to give 4,5,6,7-tetrahydro-1,3-dimethyl-3H-cyclohepta[1,2-c:4,3-c']dipyrazole.

What is claimed is:

1. A compound of the formula

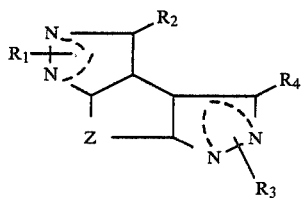

wherein $R_1$, $R_2$, $R_3$ and $R_4$ are each independently selected from hydrogen or methyl with the proviso that at least one of them must be methyl and with $R_1$ and $R_3$ being positioned on one of the nitrogens in their respective rings with the other nitrogen then being doubly bonded to the adjacent carbon; the dotted lines indicate the presence of two conjugated double bonds with the specific position of the double bonds being determined by the position of the $R_1$ or $R_3$ substituents; and Z is —(CH$_2$)n— wherein n is 2 or 3.

2. A compound according to claim 1 having the formula

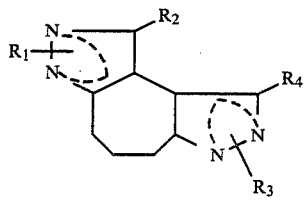

wherein $R_1$, $R_2$, $R_3$ and $R_4$ are each independently selected from hydrogen or methyl with the proviso that at least one of them must be methyl and with $R_1$ and $R_3$ being positioned on one of the nitrogens in their respective rings with the other nitrogen then being doubly bonded to the adjacent carbon; the dotted lines indicate the presence of two conjugated double bonds with the specific position of the double bonds being determined by the position of the $R_1$ or $R_3$ substituents.

3. A compounds according to claim 1 which is 4,5,6,7-tetrahydro-2,7-dimethyl-2H-cyclohepta[1,2-c:4,3-c']-dipyrazole.

4. A compound according to claim 1 which is 4,5,6,7-tetrahydro-3-methyl-3H-cyclohepta[1,2-c:4,3-c']dipyrazole.

5. A compound according to claim 1 which is 4,5,6,7-tetrahydro-3,7-dimethyl-3H-cyclohepta[1,2-c:4,3-c']-dipyrazole.

6. A compound according to claim 1 which is 3,4,5,6-tetrahydro-3,6-dimethylbenzo[1,2-c:4,3-c']dipyrazole.

7. A method for alleviating bronchial spasm in mammals which comprises administering to a mammal in need thereof a bronchodilating amount of a compound of the formula

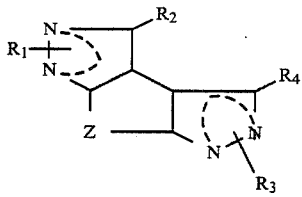

wherein $R_1$, $R_2$, $R_3$ and $R_4$ are each independently selected from hydrogen or methyl with the proviso that at least one of them must be methyl and with $R_1$ and $R_3$ being positioned on one of the nitrogens in their respective rings with the other nitrogen then being doubly bonded to the adjacent carbon; the dotted lines indicate the presence of two conugated double bonds with the specific position of the double bonds being determined by the position of the $R_1$ or $R_3$ substituents; and Z is —(CH$_2$)n— wherein n is 2 or 3.

* * * * *